United States Patent [19]

Cramer et al.

[11] Patent Number: 4,686,190
[45] Date of Patent: Aug. 11, 1987

[54] DEVICE USEFUL FOR GROWING AND/OR TESTING BIOLOGICAL MATERIALS

[75] Inventors: Eva B. Cramer, Port Washington; Linda C. Milks; Gregory P. Conyers, both of Brooklyn; Andrew Valenti, Uniondale; Antonio Perez, Flushing, all of N.Y.

[73] Assignee: The Research Foundation of State University of New York, Albany, N.Y.

[21] Appl. No.: 831,147

[22] Filed: Feb. 19, 1986

[51] Int. Cl.⁴ ............................................. C12M 1/34
[52] U.S. Cl. .................................. 435/291; 435/285; 324/444
[58] Field of Search ............... 435/284, 285, 287, 291, 435/299-301, 173; 204/403; 324/439, 444, 446, 449, 450

[56] References Cited

U.S. PATENT DOCUMENTS

3,924,175 12/1975 Wilson .................. 324/444
4,224,125 9/1980 Nakamura et al. ........ 204/403

Primary Examiner—James C. Yeung
Assistant Examiner—Noah Kamen
Attorney, Agent, or Firm—Cooper, Dunham, Griffin & Moran

[57] ABSTRACT

A device useful for the in vitro study of cell migration across a monolayer of epithelial cells while simultaneously measuring the transepithelial electrical resistance of the epithelial monolayer is provided and is characterized as including at least three components, a cylinder, a chamber and a punch. The cylinder is designed for tissue culture, the chamber provides a controlled space and/or environment for the cylinder and the punch is provided to cut the epithelial monolayer and its substrate.

30 Claims, 11 Drawing Figures

DEVICE USEFUL FOR GROWING AND/OR TESTING BIOLOGICAL MATERIALS

This invention is directed to a device useful for the growing and/or testing of biological materials. More particularly, this invention is directed to a device for the in vitro study in cell migration across a monolayer of epithelial cells while simultaneously measuring the transepithelial electrical resistance of the epithelial monolayer.

In connection with studies of chronic inflammation, particularly granulomatous diseases, such a tuberculosis, sarcoidosis and the like, it is particularly useful to have a device and techniques of employing the same which are useful for a better understanding of the process of granuloma formation as well as the effects of drug therapy thereon.

Accordingly, it is an object of this invention to provide a device and techniques employing the same for the in vitro study of growing and/or testing biological materials, particulary for the in vitro study of cell migration across a monolayer of epithelial cells.

It is another object of this invention to provide a device for the in vitro study of cell migration across a monolayer of epithelial cells while simultaneously measuring the transepithelial electrical resistance of the epithelial monolayer.

It is another object of this invention to provide a device which has in connection with the above objects the capability of the operator employing the device being able to vary the type of the migrating cell and/or the type of epithelium as well as the type of substratum on which the epithelium is grown.

How these and other objects of this invention might be achieved are set forth in the accompanying disclosure made with reference to the accompanying drawings wherein.

THE INVENTION

The invention involves a device which permits the in vitro study of cell migration across a monolayer of epithelial cells while simultaneously measuring the transepithelial electrical resistance of the epithelial monolayer. One employing the device of this invention has the option of varying the type of migrating cell and/or the type of epithelium as well as the type of substratum in which the epithelium is grown. More particularly, the device of this invention comprises in combination three elements or parts, a cylinder, a chamber and a punch. The cylinder is designed for tissue culture. The chamber is made up of a well, setup station, base. The punch, such as a stainless steel punch, is designed to precisely cut off uniform discs without damaging or separating the epithelial monolayer from the substrate and to cut out the epithelial monolayer and its substrate when the cylinder is placed on a suitable support and the punch inserted and tapped with a hammer.

DETAILED DESCRIPTION OF THE INVENTION

The device consists of three parts; the cylinder, the chamber and the punch. The cylinder is designed for tissue culture and is usefully composed of Lexan, a registered trademark for polycarbonate resin, which can be autoclaved and reused. Lexan is a polymeric material compatible with epithelial cell growth. The cells form a confluent monolayer and grow up the sides of the cylinder, forming a natural seal. Lexan is also translucent and allows visulatization of the fluid in the cylinder. Further, the cylinder is machined from one piece of Lexan which prevents separation of bonded sections.

The cylinder fits into various shaped and sized commercial tissue culture dishes. The lids of the tissue culture dishes can be placed on the culture dishes when the cylider either stands in a flat bottom tissue culture dish or multiwell that is at least 14 mm deep and larger than 20 mm in I.D., or the cylinder can hang by its rim in a smaller multiwell with I.D. of 16 mm. A slot in the rim allows easy fluid changes when the cylinders are hung in 16 mm multiwells. When the cylinder is suspended in the multiwell, fluid can reach the cells, growing on the substrate from both the apical and basal surface.

The cylinder is designed to use a variety of substrates. The outside diameter of the cylinder is 13 mm which is a standard commercial size for most filters. Millipore (cellulose acetate and nitrate) or nucleopore (polycarbonate) micropore filters can be glued to the bottom of the cylinder using a silicone adhesive sealant which is not toxic to the cells. The cylinder filter assembly can be autoclaved to provide sterility. The cylinder also allows filters of various pore sizes (0.1 $\mu$m–12.0 $\mu$m) and shapes (maze or straight) to be used. The pore size of the filters is important in determining the size cell which can migrate into the filter. A pore size of 0.45 $\mu$m excludes most cells but does allow them to accumulate on the apical surface of the filter. Pore sizes of 3.0 and 5.0 $\mu$m are used for chemotactic studies of neutrophils and monocytes, respectively.

The cylinder is designed so that amnion connective tissue can be pulled taut and securely attached to the bottom of the cylinder with a Viton O-ring (13 O.D., 10 I.D.). Viton is a registered trademark for a synthetic rubber material. The O-ring fits into a groove near the bottom of the cylinder. Viton is non-toxic to the cells and can be sterilized by autoclaving. Further, the bottom edges of the cylinder have been smoothed and rounded to prevent damage and tearing of the connective tissue. The cylinder also has a slot on one side in the groove to allow the O-ring to be removed easily. The design of the cylinder also allows other substrates to be used such as nylon mesh coated with a cross linked collagen gel, isolated epithelial sheets such as urinary bladder, mesentery and frog skin, walls of blood vessels, such as aorta, or dialysis membrane.

The cylinders can be designed in various sizes. The minimum I.D. is the spaced needed for two bridges and a needle for fluid exchange. At present, two sizes are useful (I.D. 6 or 9 mm) which hold 0.3 or 0.5 ml of fluid and exposes 0.32 or 0.71 cm$^2$ of filter surface, respectively. The Lexan material of the cylinder is resistant to aldehyde fixatives. Therefore the cells can be fixed while still attached to the cylinder. This is especially convenient for ultrastructural tracer studies where it is desirable to fix the tissue while the two compartments are still separated. The cylinder can be reused after going through a cleaning procedure which involves quenching the free aldehydes in 1M glycine. The cylinder is designed to be able to grow epithelial cells from the respiratory, digestive, urinary and reproductive tracts as well as the endothelium lining blood vessels.

Figure 1:
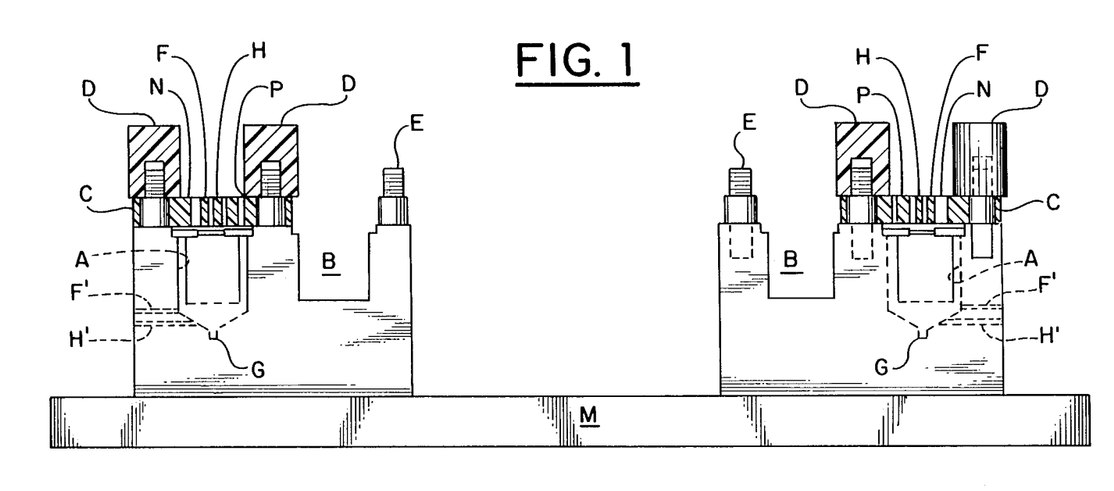
FIG. 1 shows one embodiment of the invention in which two chambers are mounted on a base. A-recording chamber; B-set-up station; C-lid; D-screw-down nut; E-threaded pins; F and F'-upper and lower compartment voltage bridge aperture, respectively; G-lower compartment fluid outlet, H and H' upper and lower compartments current bridge aperture, respectively; M-plexiglas base; N-aperture for fluid addition and removal from upper compartment; P-aperture for fluid addition to lower compartment.

The chamber which is made of Lucite, a registered trademark for a polyacrylate material, comprises a well, set-up station, base and lid. (FIG. 1) The well forms the lower of two compartments when the cylinder with attached monolayer of epithelial cells is suspended in place. (FIG. 5,A) The set-up station is used to exactly set the length of the upper compartment voltage recording brdige (F) to 1mm above the epithelial monolayer. (FIG. 5,B) The base provides stability to the assembly. The lid has four holes. The current (H) and voltage (F) bridges going to the upper compartment occupy two holes. (FIG. 5) The other two holes (N and P) are used to remove or add fluid to the upper and lower compartments, respectively, without disturbing the monolayer.

The chamber can be used for simultaneous chemotactic and transepithelial electrical resistance studies. One can vary the type of migrating cell, epithelial monolayer, substrate or the fluid in both compartments. One can study either random, chemokinetic or directed (chemotactic) migration. The chamber design enables the transepithelial electrical resistance of the cell monolayer to be determined by measuring the voltage change across the monolayer. The chamber has two holes on the side of the well to hold one voltage and one current-passing bridge for the lower compartment. (FIG. 7,H) The holes are tapered slightly to hold the bridges securely and prevent leakage. They are placed on the side so they are near the electrodes and do not interfere with viewing the lower compartment.

This construction enables the voltage bridges to be easily and precisely set at 1 mm from either surface of the epithelium. The voltage bridge for the lower compartment is set by placing the bridge in the upper hole on the side of the well and lining up the end of the bridge with the center draining hole. The top voltage bridge is positioned by placing the lid on the pegs over the setup station by placing the bridge in the center hole and pushing it down until it is stopped at the flat surface of the set-up station. The bridge length is such that it will be precisely 1 mm above the apical surface of the epithelium when the lid with the bridge is moved to the pegs on either side of the well.

Figures 4, 5, 6, 7, 8:
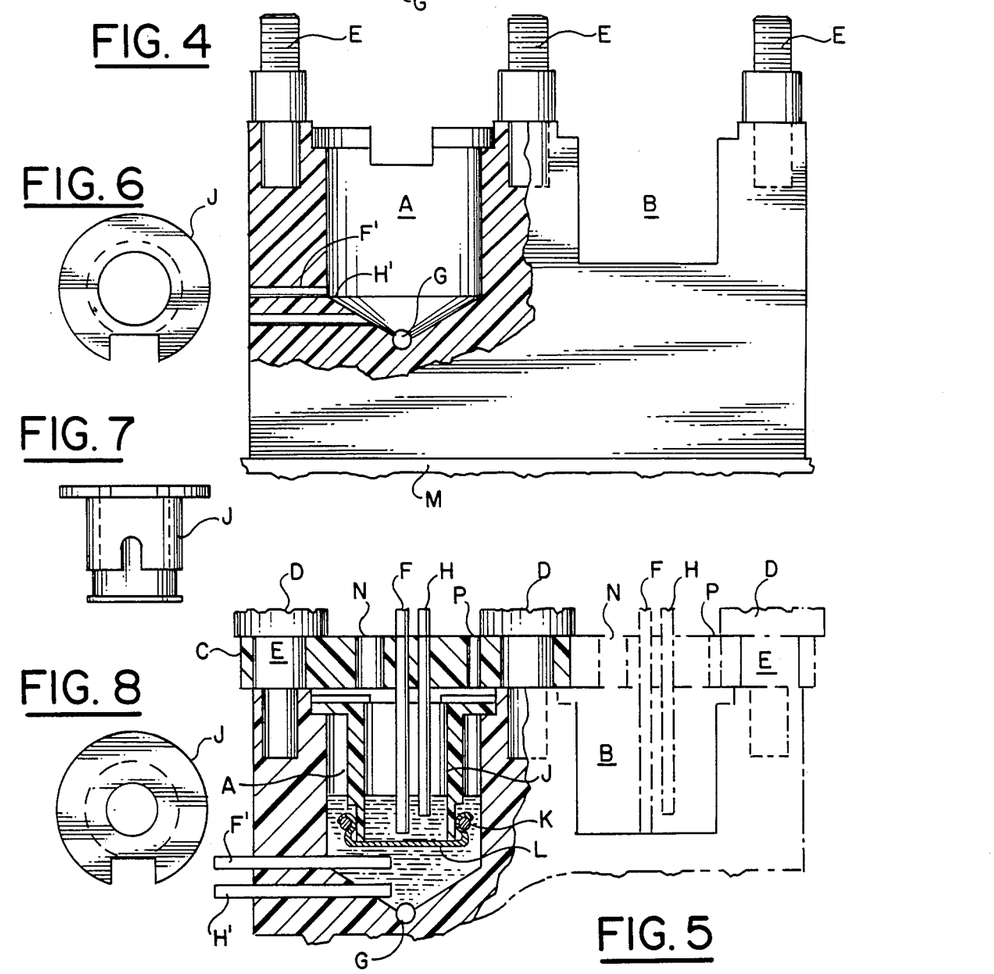
FIG. 4 is a side view of the chamber shown in FIG. 3. A-recording chamber; B-set-up station; E-delrin pin; F'-lower compartment voltage bridge aperture; G-lower compartment fluid outlet; H'-lower compartment current bridge aperture.
FIG. 5 is a side view of the chamber shown in FIG. 3 with the cylinder (J), lid (C), delrin pins (E) and screw-down nuts (D) in place. Voltage and current bridges are in place at F and F' and H and H', respectively. Viton O-ring (K) is in place around cylinder holding substrate (L) onto cylinder bottom. G-lower compartment fluid outlet. The right side of the figure shows set-up chamber (B) with voltage (F) and current (H) bridges in place.
FIG. 6 is a top view of one embodiment of the cylinder (J) with a large inside diameter.
FIG. 7 is a side view of the cylinder (J) shown in FIG. 6.
FIG. 8 is a top view of one embodiment of the cylinder (J) with a small inside diameter.

Before setting-up for recording, the lid with the electrodes can be rested on the set of pegs on either side of the set-up station while cylinder samples are changed. The tapered ends of the lid enable one to change the notched round rimmed cylinder without being restricted by the resting lid. The asymmetric design of the lid easily allows one to orient the bridge and fluid changing apertures in the correct direction. When the chamber is assembled, the design of the lid and chamber are such that fluid changes can be made without disturbing the monolayer. The lid is held in place by two delrin pins and nuts (FIG. 5, E and D). The well of the chamber (FIG. 1,A) is conical shaped with a drainage hole at the bottom (FIG. 1,G) which exits through the front of the chamber. Teflon, a regisered trademark for a polyfluororesin, tubing with an attached syringe is inserted into the exit pathway to prevent leakage and to remove fluid.

As previously mentioned, the chamber has holes in the lid which enable one to add and remove fluid from the upper compartment and add fluid to the lower compartment. When the slot in the rim of the cylinder is positioned beneath the fluid hole (FIG. 1, P), a needle inserted into this hole can reach the lower compartment. The chamber has space between the well and the cylinder walls to enable bubbles trapped beneath the cylinder to escape when the chamber is tipped. It is designed so that the top surface of the well has a cylindrical depression which matches the cylinder rim diameter and thickness. Its purpose is to center the insert within the well and prevent it from mvoing from side to side.

Figure 2:
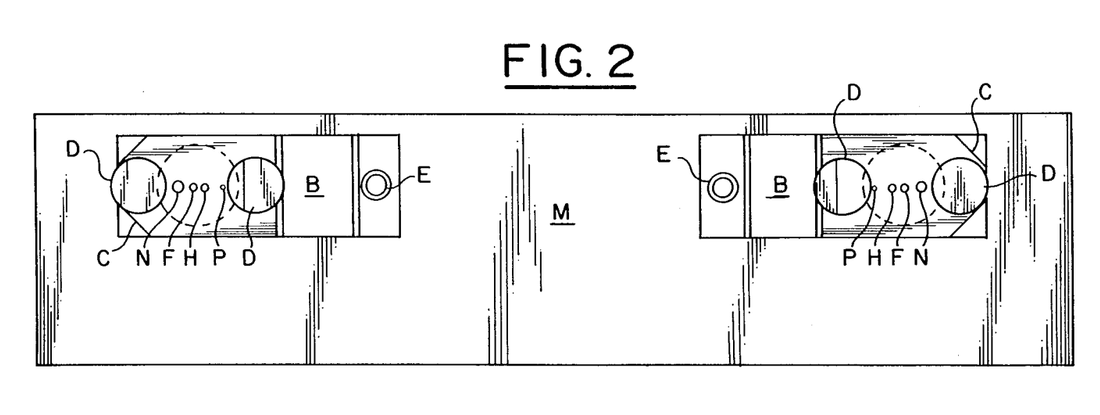
FIG. 2 is a top view of the embodiment shown in FIG. 1. B-set-up station; C-lid; D-screw-down nuts; E-threaded pins; F-upper compartment voltage bridge aperture: H-upper compartment current bridge aperture; H-plexiglas base; N-aperture for fluid addition and removal from upper compartment; P-aperture for fluid addition to lower compartment.
Figures 9, 10, 11:
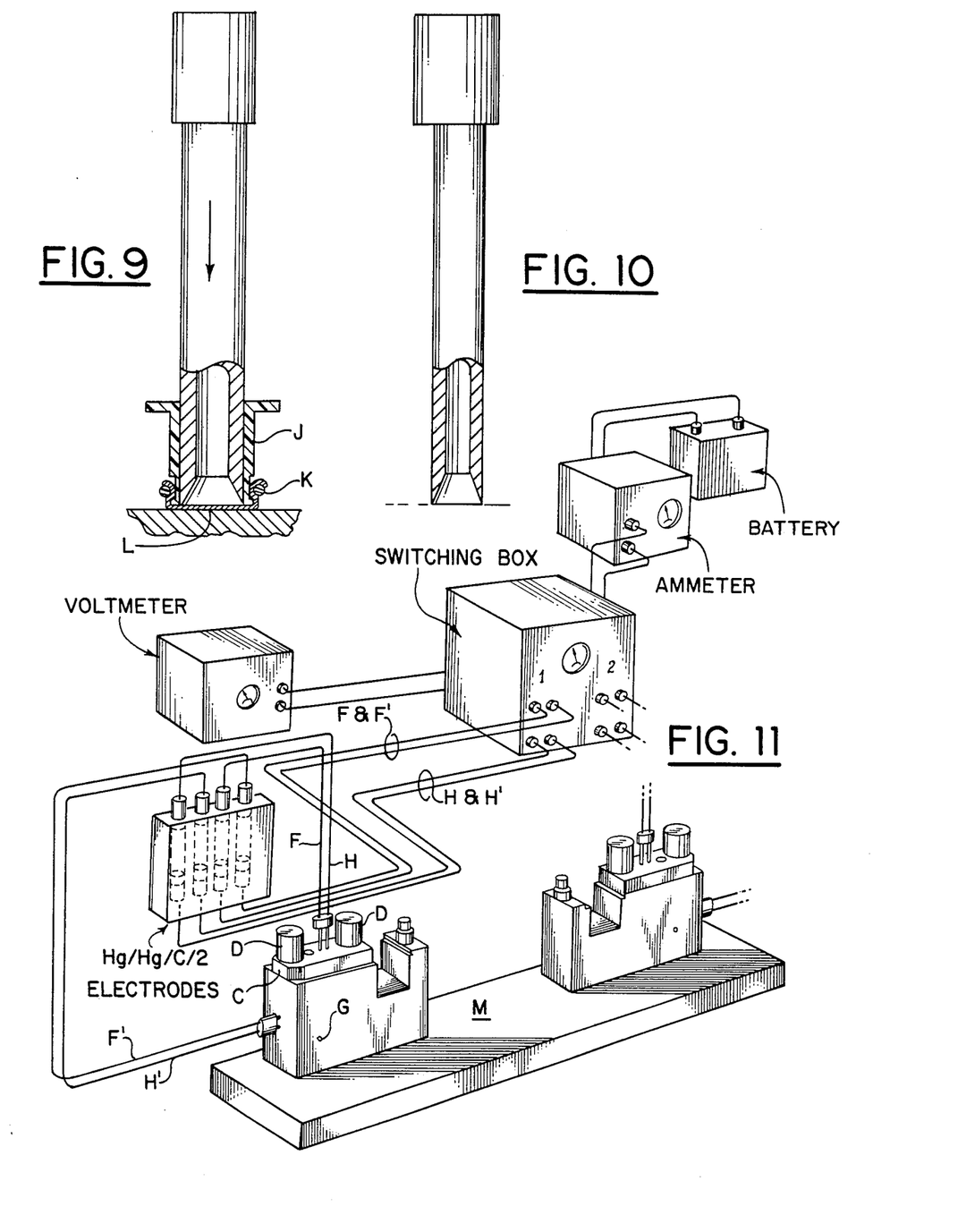
FIG. 9 is a cut away view of one embodiment of the punch, wherein the punch has been placed inside the cylinder (J) and is set to remove a plug of substrate (L) from the base of the cylinder. K-Viton O-ring.
FIG. 10 is a cut away view of a punch with a narrow outside diameter.
FIG. 11 is a view of one embodiment of the apparatus in which voltage and current bridges, F and F' and H and H', resepctively, are connected to electrodes and electrical equipment.

Chamber geometry (I.D.=15.7 mm) is such that when a large or small cylinder is filled with 0.5 or 0.3 ml, respectively, the fluid level in the upper and the lower compartments will be even when approximately 1.5 ml of fluid is added to the lower compartmtne. Equalizing the fluid levels prevents hydrostatic pressure fluctuations. As shown in the FIGS. 1, 2 and 11, the apparatus can be constructed with the chambers placed as mirrored images. The two chambers are mounted on a block of plexiglas (M) for support. This design enables two set-ups to run simultaneously.

The punch is made of stainless steel in two O.D.'s which fit the I.D. of the two different sized cylinders. It is designed to precisely cut uniform disks of tissue on substrate without damaging or separating the epithelial monolayer from the substrate. The punch is designed to cut the eipthelial monolayer and its substrate when the cylinder is placed on plexiglas and the inserted punch (FIG. 9) is trapped with a hammer. The knurled head of the punch of the punch allows the punch to be securely held by hand when hitting the head with a hammer. The cutting edge of the punch is slanted to prevent damaging the epithelial monolayer, and has a cutting edge which can be resharpened.

During the process of inflammation, leukocytes such as neutrophils and monocytes adhere to and migrate across the endothelium, a type of epithelium which lines blood vessels, and frequently a second epithelium which lines an infected organ. The epithelial cells are held together by tigh junctions which form an occluding belt around the circumferene of the cells. The transepithelial electrical resistance is a measure of the permeability of these junctions. Little is known about how leukocytes are able to traverse these barriers, the effect of epithelial permeability on the migration of these cells, the effect of leukocyte migration on epithelial permeability, or the role serum and connective factors play in this process. This device would enable one to grow in vitro either endothelium or the epithelia of organs of the respiratory, digestive, urinary or reproductive tract and study the interaction of neutrophils or monocytes with any of these tissues.

Studies[23] have been carried out on the effects of biochemical compounds known as leukotrienes on endothelium and on the transendothelial migration of neutrophils. In one part of these studies human amnion tissue was attached across the bottom of a plastic cylinder. The tissue was prepared such that all connective tissue cells and epithelial cells were removed and only connective tissues remained, providing a support upon which a confident layer of human umbilical endothelial cells were grown. Transendothelial electrical resistance was measured across the confluent layer of endothelial cells. Further, neutrophil migration across the endothelial layer was studies in response to leukotriene stimulation. The connective tissue support layer and attached endothelial tissue was prepared for viewing in cross-section under the electron microscope, and neutrophils were observed in migration through the endothelial cell layer.

These studies can be performed in the absence of serum and connective tissue factors so that one can examine the direct effect of leukocytes on the integrity of endothelium or epithelium. One then has the option of adding various serum and connective tissue components in the absence and presence of leukocytes to investigate the specific as well as the cumulative effect of these factors.

The device is designed so that one can simultaneously examine the interaction of two different cell types from a physiological, biochemical and morphological perspective. While the rapid migration of leukocytes to sites of inflammation is a very important defense mechanism in the body, sometimes the accumulation of leukocytes can be destructive. This is observed in diseases such as rheumatoid arthritis, glomerulonephritis and emphysema. This device can be used in the development of antiinflammatory drugs which either prevent the accumulation of leukocytes or interfere with their destructive properties. In addition, the device can be used to develop drugs which either cause or prevent increased vascular or epithelial permeability.

One need not always use the system to simultaneously study chemotaxis and epithelial permeability. One can use the device to grow endothelium and determine its transepithelial electrical resistance. This information will provde the research with a measure of the confluency and permeability of the monolayer without disturbing the cells. The tissue can then be used to study the process of metastasis. Relatively little is known about how or why certain cancer cells leave a primary tumor and migrate to another organ. In many ways this process is analogous to the migration of leukocytes and like leukocytes the cancer cells must also cross the endothelium.

Tumor cells leaving the primary tumor migrate into the blood by crossing the endothelium from the basal to the apical surface. They circulate in the blood stream and eventually leave the vasculature by crossing the endothelium, apically to basally, and develop in a new location.

The system is designed so that one can examine both aspects of the migratory process and perhaps determine ways to prevent it. In addition one can grow tumors in the connective tissue on which the endothelium is grown and examine how the metastasizing cells leave the primary site. One can also grow normal tissue from organs commonly involved in metastasis in the connective tissue beneath the monolayer of endothelial cells. This will provide a way to determine if there are attractants or growth factors in these organs which stimulate the accumulation and growth of tumor cells.

The migration of monocytes across endothelium can be observed during the process of atherosclerosis by growing an artificial vessel wall and studying the migration of monocytes into the vessel wall and their subsequent development into foam cells.

The system can also be modified to study chronic inflammation. Granulomatous diseases such as tuberculosis, sarcoidosis, schistosomiasis, leprosy and silicosis are major causes of morbidity and mortality worldwide. Foreign body granuloma can be formed by the addition of human peripheral monuclear cells to the apparatus with attached amnion connective tissue containing an absorbable synthetic suture. The device of this invention provides a way to study the process of granuloma formation, organization and repair, as well as the effects of drug therapy.

The process of inflammation is quite complex. It involves hemodynamic changes, increases in vascular permeability, and leukocyte exudation. Relatively little is known about the factors or mediators that control this phenomenon. Both slow-reacting substance (SRS), which consists of cysteine-containing 5(S)-Hydroxy-6(R)-S-gluthathionyl-7,9-trans-11,14-cis-eicosatetraenoic acid ($LTC_4$), 5(S)-Hydroxy-6(R)-cysteinylglycyl-7,9-trans-11,14-cis-eicosatetraenoic acid ($LTD_4$), and 5(S)-Hydroxy-6(R)-cysteinyl-7,9-trans-11,14-cis-eicosatetraenoic acid ($LTE_4$), and 5(S)12(R)-Dihydroxy-6,24-cis-8,10-trans-eicosatetraenoic acid ($LTB_4$) have been implicated in this process, $LTC_4$ and $LTD_4$ are vasoactive compounds that have been shown to produce transient constriction of arterioles and exudation from postcapillary venules in the hamster cheek pouch[1] as well as rapid, transient pulmonary and systemic hypertension followed by a prolonged fall in blood pressure and decreased cardiac output in monkeys[2]. The closely related $LTB_4$ stimulates white cell adhesion and extravasation in vivo[3-5] and neutrophil chemotaxis in vitro.[5-7] In addition, concentrations of LTB$_4$ higher than those required for chemotaxis stimulate edema formation and enzyme release from leukocytes.[6,8] How these compounds mediate their effects, however, is relatively unknown.

To determine possible mechanisms for the vasoactive actions of SRS, the effects of LTC$_4$, LD$_4$, and LTE$_4$ on arachidonic acid (20:4) metabolism in endothelium were examined. Human endothelial cells were isolated from umbilical veins by collagenase treatment according to the method of Jaffe et al.[9] Cells became confluent 3 to 4 days after plating. Experiments were performed on cells of either primary, first, or second passage. All cells examined contained factor VIII antigen as determined by indirect immunofluorescence.[10] As shown by Wagner et al.,[11] factor VIII antigen was apparent in the perinuclear region and in small rodlike structures throughout the cytoplasm.

To determine if SRS stimulated 20:4 metabolism in endothelium, each 35 mm dish of endothelial cells was washed in phosphate-buffered saline and was labeled with 1.0 $uCi[^3H]$20:4(91.2 Ci/nmol; New England Nuclear, Boston, Mass.) in 1 ml medium 199 containing 10% heat-inactivated human serum. After 16 hours, the cells were washed three times with phosphate-buffered saline solution, placed in medium 199 with the appropriate stimulus, and incubated at 37° C. Duplicate 50 μl aliquots of medium were removed at 10, 20, 30, and 60 minutes for radioactivity measurements as determined by liquid scintillation counting in Hydrofluor. Endothelial cells remained viable after a 60-minute exposure to LTC$_4$ as assessed by trypan blue exclusion. At this time the culture medium was removed and cells were washed with phosphate-buffered saline solution and scraped into 1 ml 0.5% Triton X-100. Duplicate aliquots were assayed for protein[12] and tritium.

As previously reported,[13] LTC$_4$ at a concentration of $10^{-9}$M caused little or no release of radiolabel above control levels. Maximal release occurred with $10^{-8}$M to $10^{-6}$M LTC$_4$. At 30 minutes, $10^{-7}$M LTC$_4$ caused approximately 6% of the incorporated radiolabel to be released. This represented a release of radiolabel that was 400% of that observed in control cultures. Although the amount of radiolabel released varied with LTC$_4$ concentration, the time course of tritium release was quite similar. LTC$_4$ caused an increase in radiolabel release that reached maximum at 30 minutes.

At 60 minutes, the medium was extracted by the method of Unger et al.[14] and total 20:4 metabolites were separated by reverse-phase High-pressure liquid chromatography (HPLC). As observed previously[13] cyclooxygenase products eluted between 4 and 16 minutes and constituted about half (52.8%±9.3%, n=6) of the recovered radiolabel. Unreacted 20:4 (elution time 111 to 150 minutes) represented the second major peak, with approximately one third (32.7% ±11.1%, n=6) of the released radiolabel, while lipoxygenase products (elution time 17 to 110 minutes) represented only approximately one seventh (14.8%±4.6%) of the released radiolabel. Control cultures released less radiolabel but produced a similar 20:4 metabolite profile.

The pooled cyclooxygenase products were rechromatographed on a Waters fatty acid analysis column to separate individual metabolites.[15] The major cyclooxygenase product was 6-keto-PGF$_1$α, the breakdown product of protacyclin. In five separate experimetns, 6-keto-PGF$_1$α represented approximately 62.2%±7.6% of radiolabeled cyclooxygenase products, while a smaller peak of PGF$_2$α averaged 11.6%±4.6%. A peak of PGE$_2$ (0% to 4%) was occasionally observed. Therefore, of the total released radiolabel, 63.3% was metabolized and 33% was converted to prostacyclin.

To determine if the three leukotrienes that comprise SRS equally stimulated 20:4 metabolism in endothelial cells, endothelial cultures were agin prelabeled with [$^3$H]30:4. Cells were exposed to $10^{-7}$M to $10^{-9}$M concentrations of LTC$_4$, LTD$_4$, and LTE$_4$ and percent of released radiolabel was calculated. Maximal release of radiolabel was obtained with $10^{-7}$M LTC$_4$ and LTD$_4$. Percent released in response to $10^{-7}$M LTC$_4$ was consistently higher than that released in response to $10^{-7}$M LTD$_4$. In fact, LTC$_4$ promoted a higher level of release than did LTD$_4$ at all concentrations ($10^{-9}$M to $4\times10^{-7}$M) tested. In contrast, LT$_4$ at concentrations up to $10^{-6}$M failed to promote an increase in tritium release above control values. Likewise, $10^{-6}$M to $10^{-7}$M LTB$_4$ was ineffective in stimulating radiolabel release by endothelial cells.

As observed for LTC$_4$, the major 20:4 metabolite synthesized byendothelial cells in response to LTD$_4$ was prostacyclin. Thus the relative effectiveness of the leukotrienes (LTC$_4$>LTD$_4$>>>LTE$_4$=LTB$_4$) indicated that specific structural features of the leukotriene molecule are necessary to promote prostacylcin synthesis. Removal of the glutamyl residue from LTC$_4$ (conversion of LTC$_4$ to LTD$_4$) caused an approximate 50% loss in prostacyclin-stimulating activity and removal of the glycyl moiety (conversion of LTD$_4$ to LTE$_4$) rendered the molecule inactive. The need for the peptide backbone was further indicated by the fact that LTB$_4$ was also ineffective in stimulating prostacyclin synthesis.

It was clear from the above studies that LTC$_4$ and LTD$_4$ increased 20:4 metabolism in endothelium and that LTC$_4$ did not. While LTB$_4$ does not appear to have an effect on 20:4 metabolism in endothelium, LTB$_4$ is a potent chemoattractant for human neutrophils. To test the chemotactic activity of our synthetic LTB$_4$, human neutrophils were isolated from citrated peripheral blood of normal volunteers by Ficoll/Hypaque and dextran sedimentation techniques.[16] The resulting cell fraction contained approximately 98% neutrophils, with 98% to 99% viability as determined by trypan blue exclusion. Before use, the neutrophils were suspended in Gey's balanced salt solution with 2% bovine serum albumin, penicillin, 63 U/ml, and streptomycin, 138 g/ml. The chemotaxis assay was performed in a 48-well microchemotaxis chamber (Neuroprobe; Bethesda, Md.) according to the method of Harvath et al.[17]. Neutrophils were stimulated to traverse the 10 μm thick polyvinylpyrrolidine-free polycarbonate filter (3 μm pore) by the addition of $10^{-6}$M to $10^{-9}$M LTB$_4$ or $10^{-7}$M f-Met-Leu-Phe (Peninsula Laboratories, San Carlos, Calif.) to the lower compartment. After a 16-minute incubation at 37° C. in a 95% air/5% CO$_2$ incubator, nonmigrating neutrophils were removed from the apical surface of the filter and neutrophils that had migrated to the lower filter surface were stained with hematoxylin. Four oil immersion fields (97X) were counted per well and the mean ±SEM of each experimental group was determined from seven wells. The number of neutrophils responding to various concentrations of LTB$_4$ were compared to those responding to $10^{-7}$M f-Met-Leu-Phe and Gey's balanced salt solution. LTB$_4$ at a concentration of $10^{-9}$M elicited a neutrophil chemotactic response significantly greater ($p<0.0005$) than random migration. Maximal neutrophil migration occurred at $10^{-7}$M LTB$_4$. This response was significantly greater ($p<0.0005$) than that evoked by $10^{-7}$M f-Met-Leu-Phe. The chemotactic response to $10^{-6}$M LTB$_4$ was significantly lower ($p<0.0005$) than that cuased by $10^{-7}$M LTB$_4$ but was similar in magnitude to that evoked by $10^{-8}$M LTB$_4$.

Figure 3:
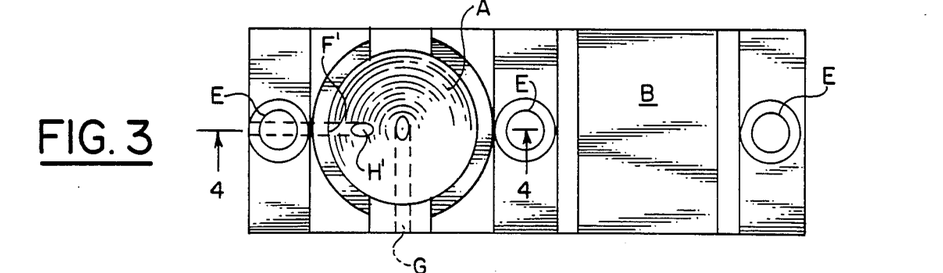
FIG. 3 is a top view of one chamber showing the recording chamber (A), E-threaded pins, the fluid outlet (G), voltage (F') and current (H') bridge apertures for lower compartment and the set-up station (B).

Although LTB$_4$ has been reported to stimulate adherence and migration of neutrophils across postcapillary venules and larger venules,[3] it was not clear if it was directly responsible for this response. In attempting to answer this quenstion, there was used an in vitro model based on a system developed for the transepithelial migration of leukocytes,[18] also studies that used amnion connective tissue[19], and another model system[20]. The system employed involved growing human umbilical vein endothelial cells on connective tissue derived from human amnion. The amnion was separated from the chorion and attached to the bototm of plastic cylinders (inner diameter 9.5 mm) with the amnion epithelium facing outward. Cylinders were submerged for 2 hours in 0.25M NH$_4$OH to destroy any possible connective tissue cells (although none have been observed) and the amnion epithelium. The amnion epithelium was scraped off with cotton swabs and cell-free connective tissue was extensively washed in phosphate-buffered saline solution and preincubated in medium 199 with 20% heat-inactivated human serum for 1 hour. Primary or first-passaged human umbilical endothelial cells ($5 \times 10^5$ cells/ml) were plated onto the connective tissue surface. Cells were fed every other day with medium 199 with 205 heat-inactivated human serum. Six to seven days after plating, the cells formed a thin confluent monolayer with transendothelial electrical resistance (a measure of endothelial permeability) as high as 50 ohms cm$^2$. Endothelial cultures were washed three times with medium 199 before each experiment. Neutrophils, suspended in medium 199 at $3.6 \times 10^6$ cells/ml, were added to the upper compartment and were stimulated to traverse endothelium and underlying connective tissue for 30 minutes in response to $10^{-7}$M synthetic LTB$_4$. At 5, 10, and 30 minutes after the addition of the neutrophils, cylinders were removed from the 37° C. incubator, washed three times in medium 199 to remove nonadherent neutrophils, and fixed in 2.5% glutaraldehyde in 0.1M phosphate buffer (pH 7.3). Tissue was postfixed ion 1% osmium tetroxide in 0.1M phosphate buffer (pH 7.3), dehydrated, and embedded in Epon 812. One-micron cross sections were made and the number of neutrophils that adhered to or migrated across each millimeter of endothelium was determined. At 5 minutes, a few neutrophils were adherent to the endothelial surface (2.6±0.4 neutrophils/mm endothelium) and a few neutrophils had started to migrate across the endothelium (1.3±0.4 neutrophils/mm endothelium). After 10 minutes, there was a significant increase in both neutrophil adherence to (33.0±6.1 neutrophils/mm endothelium) and migration across (45.0±5.6 neutrophils/mm endothelium) the endothelium. Examination of the tissue by transmission electron microscopy revealed neutrophils adherent to the apical endothelial surface, in the process of traversing the endothelium, and caught between the basal surface of the endothelium and the endothelial basal lamina (FIG. 3). After 15 minutes of incubation, neutrophils had penetrated the basal lamina and by 20 minutes they had migrated deeper into the connective tissue. At 30 minutes there was a decline in the number of neutrophils adherent to the nedothelial surface (19.2±1.0 neutrophils/mm endothelium), whereas the number that had accumulated in the connective tissue (240.0±18.1 neutrophils/mm endothelium) was now approximately 500% that observed at 10 minutes. Thus, in the absence of serum and connective tissue factors, LTB$_4$ was quite capable of stimulating neutrophil adherence to and migration across endothelium.

The ability of $10^{-7}$M f-Met-Leu-Phe and LTB$_4$ to stimulate transendothelial migration of neutrophils was observed. As had been seen inthe micropore filter chemotactic assay, LTB$_4$ was again able to stimulate significantly ($p<0.0005$) more neutrophils to undergo chemotaxis and to traverse endothelium than were stimulated by f-Met-Leu-Phe.

Tests are carried out to study the effects of leukotrienes on human endothelium and on the transendothelial migration of human neutrophils. Results thus far indicate the LTC$_4$ and LTD$_4$ ($10^{-6}$M to $10^{-8}$M) promote endothelial cells to metabolize 20:4 and that the major metabolite formed was prostacyclin. Unlike thrombin[21] and histamine,[22] which produce maximal levels of prostacyclin release within 10 minutes, LTC$_4$ and LTD$_4$ induced prostacyclin synthesis over an approximate 30-minute period. Direct comparisons of LTC$_4$, LTD$_4$, LTE$_4$, and LTB$_4$ on a molar basis indicate that LTC$_4$ was approximately 50% more effective than LTD$_4$ in stimulating prostacyclin synthesis and that LTE$_4$ and LTB$_4$ were ineffective. And finally, it was possible through the use of an in vitro model system to demonstrate that LTB$_4$ was able to stimulate neutrophil adherence to and migration across an endothelial monolayer in the absence of serum and connective tissue factors, thus suggesting that LTB$_4$ is able to directly mediate these events.

REFERENCES

1. Dahlen S-E, Bjork J, Hendquist P, Arfors K-E, Hammarstrom S, Lindgren J-A, Samuelsson B: Leukotrienes promote plasma leakage and leukocyte adhesion in postcapillary venules. In vivo effects with relevance to the acute inflammatory response. Proc Natl Acad Sci USA 78:3887, 1981
2. Smedegaard G, Hedquist P, Dahlen S-E, Revenas B, Hammerstrom S, Samuelsson B: Leukotriene C$_4$ affects pulmonary and cardiovascular dynamics in monkey. Nature 295:327, 1982.
3. Lindbom L, Hedqvist P, Dahlen S-E, Lindgren J-A, Arfors K-E: Leukotriene B4 induces extravasation and migration of polymorphonuclear leukocytes in vivo. Acta Physiol Scand 116:105, 1982.
4. Bray MA, Ford-Hutchinson AW, Smith MJH: Leukotriene B$_4$: an inflammatory mediator in vivo. Prostaglandins 22:213, 1981.
5. Lewis RA, Goetzl EJ, Drazen JM, Soter NA, Austen KF, Corey EJ: Functional characterization of synthetic leukotriene B and its sterochemical isomers. J Exp Med 154:1243, 1981.
6. Palmblad J, Malmsten C, Uden A-M, Radmark O, Samuelsson B: Leukotriene B$_4$ is a potent and sterospecific stimulator of neutrophil chemotaxis and adherence. Blood 58:658, 1981.
7. Goetzl EJ, Pickett WC: Novel structural determinants of the human neutrophil chemotactic activity of leukotriene B. J Exp Med 153:482, 1981.
8. Bjork JH, Hedqvist P, Arfors K-E: Increase in vascular permeability induced by leukotriene B$_4$ and the 9. Jaffe EA, Nachman RL, Becheer CG, Minick CR: Culture of human endothelial cells derived from umbilical veins. J Clin Invest 52:2745, 1973.
10. Jaffe EA, Hoyer LW, Nachman RL: Synthesis of antihemophilic factor antigen by cultured human endothelial cells. J Clin Invest 52:2757, 1973.
11. Wagner DD, Olmsted JB, Marder VJ: Immunolocalization of von Willebrand protein in Weibel-Palade bodies of human endothelial cells. J Cell Biol 95:355, 1982.
12. Lowry OH, Rosebrough NJ, Farr AL, Randall RJ: Protein measurement with Folin phenol reagent. J Biol Chem 193:265, 1951.
13. Cramer EB, Pologe L, Pawlowski NA, Cohn ZA, Scott WA: Leukotriene C promotes prostacyclin synthesis by human endothelial cells. Proc Natl Acad Sci USA 80:4109, 1983.
14. Unger WG, Stanford IF, Bennett A: Extraction of protaglandins from human blood. Nature 233:336, 1971.
15. Alan I, Ohuchi K, Levine L: Determination of cyclooxygenase products and prostaglandin metabolites using high pressure liquid chromatography and radioimmunassay. Anal Biochem 93:339, 1979.
16. Boyum A: Isolation of mononuclear cells and granulocytes fromhuman blood: isolation of mononuclear cells by one centrifugation, and of granulocytes by combining centrifugation and sedimentationat 1G. Scand J Clin Lab Invest [Supp]21:77, 1968.
17. Harvath L, Falk W, Leonard E: Rapid quantitation of neutrophil chemotaxis: use of a polyvinylpyrrolidone-free polycarbonate membrane in a multiwell assembly. J Immunol Methods 37:39, 1980.
18. Cramer EB, Milks L, Ojakian g: Trnasepithelial migration of human neutrophils: An in vitro model system. Proc Natl Acad Sci USA 77:4069, 1980.
19. Folz CM, Russo FG, Siegal GP, Terranova VP, Liotta LA: Interactions of tumor cells with whole basement membrane in the presence or absence of endothelium. Prog Clin Biol Res 89:353, 1982.
20. Furie MB, Cramer EB, Naprstek BL, Siverstein SC: Cultured endothelial cell monolayers that restrict the transendothelial passage of macromolecules and electrical current. J Cell Biol 98:103, 1984.
21. Weksler BB, Ley CW, Jaffe EA: Stimulation of endothelial call prostacyclin production by thrombin, trypsin and ionophore A23187. J Clin Invest 62:923, 1978.
22. Baenziger NL, Force LE, Becherer PR: Histamine stimulates prostacyclin synthesis in cultured human umbilical vein endothelial cells. Biochem Biophys Res Commun 92:1435, 1980.
23. Cramer EB, Migliorisi, g, Pologe, G, Abrahams, E, Pawlowski, E, Cohn, Z, Scott, WA: Effect of Leukotrienes on Endothelium and the Transendothelial Migration of Neutrophils. J Allerg & Clinc Immun 74:386, No. 3, Part 2, 1984.

What is claimed is:

1. An apparatus useful for the study of biological cell migration and for the measurement of electrical resistance across a monolayer of cells which comprises, an internal chamber, an external chamber, said internal chamber being a cylinder open at both ends, a substrate provided across and attached to one end of said internal chamber on which are growing a confluent layer of cells, said internal chamber being positioned within said external chamber such that said layer of cells on said substrate is contacted by a first fluid or solution at its basal aspect and by a second fluid or solution at its apical aspect within said chambers so that an electrical current may flow through said substrate and layer of cells, a pair of bridges consisting of one current passing bridge and one voltage recording bridge positioned above said layer within said internal chamber and an identical pair of said bridges located below said layer and substrate within said external chamber, said pair of bridges connected to circuit means for measuring voltage across said layer.

2. An apparatus of claim 1 wherein the cells are eptithelial cells.

3. An apparatus of claim 1 wherein the cells are endothelial cells.

4. An apparatus of claim 1 wherein the internal chamber is composed of a plastic.

5. An apparatus of claim 4 wherien the internal chamber is composed of Lexan.

6. An apparatus of claim 4 wherein the internal chamber is composed of Lucite.

7. An apparatus of claim 1 wherein the internal chamber is composed of glass.

8. An apparatus of claim 1 wherein the external chamber is composed of a plastic.

9. An apparatus of claim 9 wherein the external chamber is composed of Lexan.

10. An apparatus of claim 9 wherein the external chamber is composed of Lucite.

11. An apparatus of claim 1 wherein the external chamber is composed of glass.

12. An apparatus of claim 1 wherein said substrate provides a surface composed substantially of cellulose acetate or cellulose nitrate.

13. An apparatus of claim 1 wherein said substrate provides a surfce composed substantially of polycarbonate.

14. An apparatus of claim 1 wherein said substrate provides a surface composed substantially of connective tissue.

15. An apparatus of claim 1 wherein said internal chamber is positioned within the external chamber such that said first fluid or solution and one pair of bridges, consisting of one current passing bridge and one voltage recording bridge are isolated from said second fluid or solution and an identical pair of said bridges located within said external chamber.

16. An apparatus for the study of biologcial cell migration and for the measurement of electrical resistance across a monolayer of cells which comprises an internal chamber, an external chamber, said internal chamber being composed of a translucent or transparent material in the form of a hollow cylinder, a lip around the top outer edge of said cylinder, a groove in the lower outer edge of said internal cylinder, said groove being capable of holding an O-ring, and O-ring provided in said groove, a substrate stretched across the lower end of said internal cylinder held in place by said O-ring and on which are cells, said external chamber consisting of a well, a set-up station, a base and a lid, said well being in the shape of a hollow cylinder which tapers conically at one end, the material making up said hollow cylinder being transparent, said well of said cylinder provided with apertures for the egress of fluid at its conical tip, a current passing bridge and a voltage recording bridge provided within the tapered conical portion at said one end of said hollow cylinder, said well of said external chamber provided with means for holding a cylinder suspended inside the well, said lid being held in place by pins and screw-down nuts, said lid providing apertures for the introduction of fluids to said well and for the introduction and removal of fluid from the internal chamber and in which are located a pair of bridges consisting of one current passing bridge and one voltage recording bridge for said internal chamber, a set-up station adjacent to said well such that when said lid is placed on said threaded pins provided on either side of said chamber, accurate and reproducible setting of one voltage recording bridge for said internal chamber positioned within said external chamberis achievable so that as said layer of cells is contacted by a first fluid or solution at its basal aspect, and by a second fluid or solution at its apical aspect an electrical current flows therethrough and voltage measurement is recorded across said cell layer by said pair of bridgges consisting of one current passing bridge and one voltage recording bridge is positioned above said cell layer within said internal chamber and an identical pair of said bridge is located below said cell layer within said external chamber.

17. An apparatus of claim 16 wherein the cells are eplithelial cells.

18. An apparatus of claim 16 wherein the cells are endothelial cells.

19. An apparatus of claim 16 wherein the internal chamber is composed of a plastic.

20. An apparatus of claim 16 wherein the internal chamber is composed of Lexan.

21. An apparatus of claim 16 wherein the internal chamber is composed of Lucite.

22. An apparatus of claim 16 wherein the internal chamber is composed of glass.

23. An apparatus of claim 16 wherein the external chamber is composed of a plastic.

24. An apparatus of claim 16 wherein the external chamber is composed of Lexan.

25. An apparatus of claim 16 wherein the external chamber is composed of Lucite.

26. An apparatus of claim 16 wherein the external chamber is composed of glass.

27. An apparatus of claim 16 wherein said substrate provides a surface composed substantially of cellulose acetate or cellulose nitrate.

28. An apparatus of claim 16 wherein said substrate provides a surface composed substantially of polycarbonate.

29. An apparatus of claim 16 wherein said substrate provides a surface composed substantially of connective tissue.

30. A chamber useful for the study of biological cells, said chamber comprising as well, a set-up station, a base, a lid, said well being made of transparent material and being open at it upper end for the introduction of fluid thereinto and provided with an apertureat its lower end for the removal of flud, said well also being provided with apertures inw hich are located of a pair of electrical bridges consisting of one current passing bridge and one voltage recording bridge into the bottom of the well of said chamber, means for holding said lid in place, said lid being provided with apertures for the introduction and removal of fluids and in which are located of a pair of bridges into said well consisting of one current passing bridge and one voltage recording bridge and means associated with said lid to provide for a predtermined orientation of said voltage recording bridge in which lid is placed on said set-up station which is attached to said base.

* * * * *